(12) United States Patent
Buczek

(10) Patent No.: US 6,736,360 B1
(45) Date of Patent: May 18, 2004

(54) ROTARY JOINTED ARM FOR A SURGICAL TRAY

(75) Inventor: Mark J. Buczek, Oceanside, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/411,517

(22) Filed: Apr. 10, 2003

Related U.S. Application Data

(60) Provisional application No. 60/442,928, filed on Jan. 27, 2003.

(51) Int. Cl.$^7$ ................................................. E04G 3/00
(52) U.S. Cl. ............................... 248/276.1; 248/278.1; 312/209
(58) Field of Search ........................... 248/276.1, 278.1, 248/282.1, 283.1, 584; 606/171, 167, 4, 5, 6, 10, 19; 312/209, 223.1, 223.2

(56) References Cited

U.S. PATENT DOCUMENTS

| | | | |
|---|---|---|---|
| 4,913,396 A | * 4/1990 | Dalebout et al. ........... 248/649 |
| 4,989,698 A | * 2/1991 | Dony ......................... 188/300 |
| 5,056,866 A | * 10/1991 | Tobler ...................... 297/303.3 |
| 5,398,622 A | * 3/1995 | Lubinskas et al. .......... 108/145 |
| 5,553,820 A | * 9/1996 | Karten et al. ............. 248/286.1 |
| 5,820,253 A | * 10/1998 | Scholz ........................ 362/267 |
| 5,823,120 A | * 10/1998 | Holmquist ................... 108/147 |
| D467,001 S | 12/2002 | Buczek et al. | |

* cited by examiner

Primary Examiner—Korie Chan
(74) Attorney, Agent, or Firm—Jeffrey S. Schira

(57) ABSTRACT

A movable arm for a surgical tray that is connected to the surgical console, is adjustable for height and allows for full, unlimited 360° rotation of the tray. The arm mechanism includes a movable wedge plate containing a sloped or ramped depression that cooperates with one end of a motion transfer pin. Horizontal movement of the wedge plate causes vertical movement of the pin. The other end of the pin, opposite the wedge plate, actuates a release mechanism that allows the arm on which the tray is mounted to be raised and lowered via a pressurized gas cylinder. Such a construction allows the tray to be rotated a full 360° without affecting the arm release mechanism.

4 Claims, 6 Drawing Sheets

ROTARY JOINTED ARM FOR A SURGICAL TRAY

This application claims the benefit of U.S. Provisional Patent Application No. 60/442,928, filed Jan. 27, 2003.

BACKGROUND OF THE INVENTION

This invention relates generally to the field of ophthalmic surgery and more particularly to surgical trays used with surgical consoles.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea, vitreous and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

Alternatively, disease or trauma may affect the retina or vitreous, in many cases requiring that the vitreous be removed.

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is usually replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

With respect to vitreous and/or retinal surgery, a variety of cutting devices, scissors, extrusion needles (cannulas), fragmenters or tissue manipulators may be used. Some of these devices, such as vitreous cutters, use a guillotine (axial) or reciprocating hollow cutting tube. Suction is applied to the interior of the cutting tube so that the tissue is aspirated away as it is cut.

To assist the surgeon and nurses during surgery, surgical control consoles generally include a tray that can extend outwardly from the console into the sterile field. The various instruments used during surgery can be placed on the tray when not in use. Prior art surgical trays may be adjustable in height from the sterile field, but can be rotated through only a limited arc because the external cable release mechanism for the height adjustment prevents the tray from being fully rotatable. This limits the usefulness and adjustability of the tray.

Therefore, a need continues to exist for an adjustable surgical tray that allow for full, unlimited 360° rotation of the tray.

BRIEF SUMMARY OF THE INVENTION

The present invention improves upon the prior art by providing a movable arm for a surgical tray that is connected to the surgical console, is adjustable for height and allows for full, unlimited 360° rotation of the tray. The arm mechanism includes a movable wedge plate containing a sloped or ramped depression that cooperates with one end of a motion transfer pin. Horizontal movement of the wedge plate causes vertical movement of the pin. The other end of the pin, opposite the wedge plate, actuates a release mechanism that allows the arm on which the tray is mounted to be raised and lowered via a pressurized gas cylinder. Such a construction allows the tray to be rotated a full 360° without affecting the arm height release mechanism.

Accordingly, one objective of the present invention is to provide an arm for a surgical tray that includes a movable wedge plate containing a sloped or ramped depression that cooperates with one end of a motion transfer pin.

Accordingly, one objective of the present invention is to provide an arm for a surgical tray having linkages that allow the tray to be rotated a full 360°.

Another objective of the -present invention is to provide an arm for a surgical tray having a height that is adjustable regardless of orientation.

Yet another objective of the present invention is to provide an arm for a surgical tray having linkages that allow infinite adjustability or coverage of the tray.

These and other advantages and objectives of the present invention will become apparent from the detailed description and claims that follow.

DETAILED DESCRIPTION OF THE INVENTION

Figure 1:
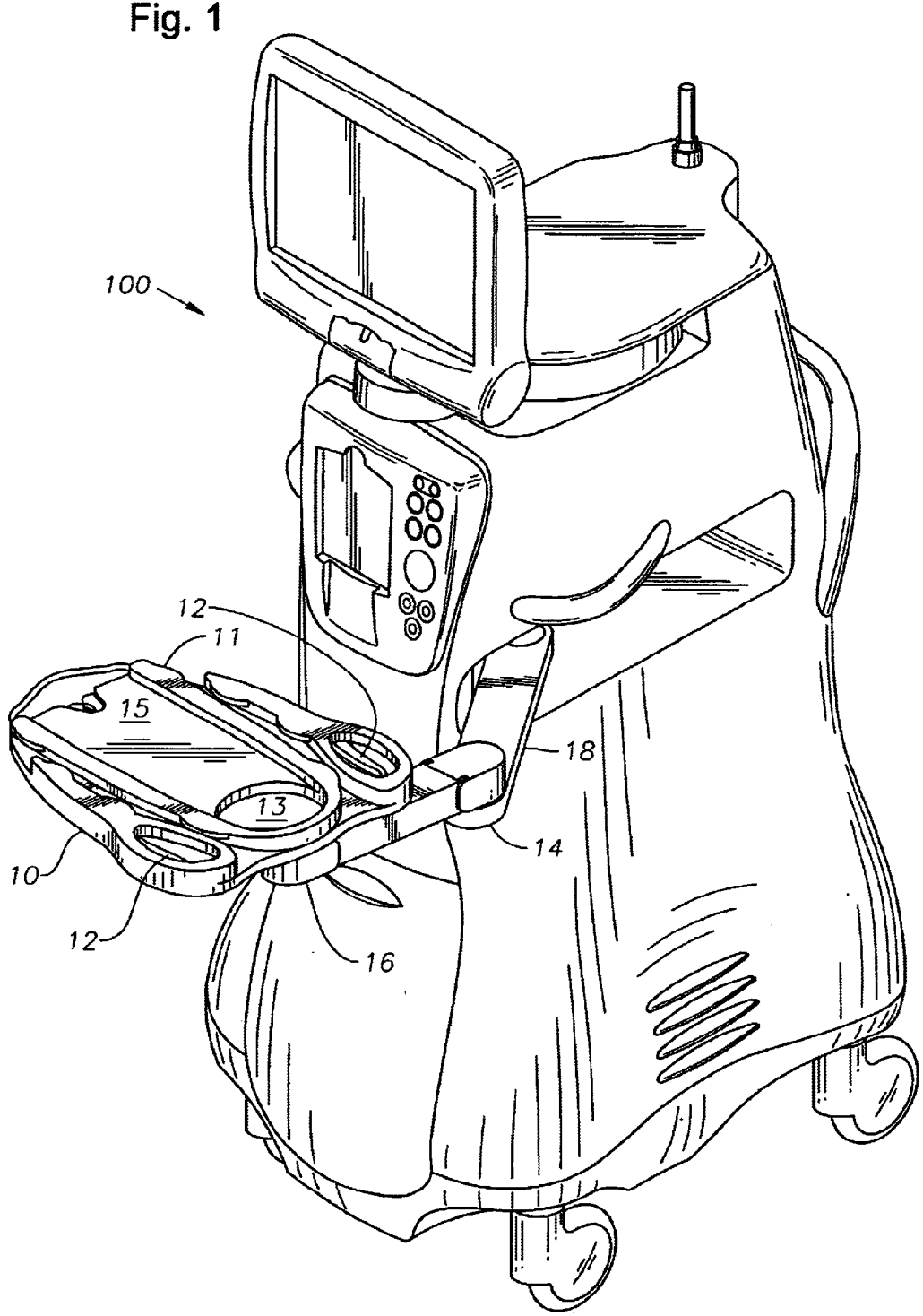
FIG. 1 is a perspective view of the arm of the present invention being used with a surgical console and having an surgical tray attached.

As best seen in FIG. 1, surgical tray 10 that can be used with the arm mechanism of the present invention generally is connected or attached to surgical console 100, such consoles being well-known in the art, although the mechanism could be made to operate independently of any other mechanism. For example, U.S. Pat. No. Des. 467,001, the entire contents of which being incorporated herein by reference, discloses a surgical console suitable for use with tray 10 of the present invention. Tray 10 generally contains body 11 that is rectangular in shape with one or more arm actuation grab handles 12 accessible from the sterile field. Body 11 may also have one or more recesses 15 to accommodate various handpieces and tools used during a surgical procedure and a recess 13 for a remote input device (not (shown). Tray 10 is connected to console 100 by arm mechanism 14. Preferably, tray 10 is centrally mounted on console 100 so that tray 10 can be accessed from either side of console 100. Tray 10 is preferably made in one or more assembled pieces from a suitable thermoplastic.

Figure 2:
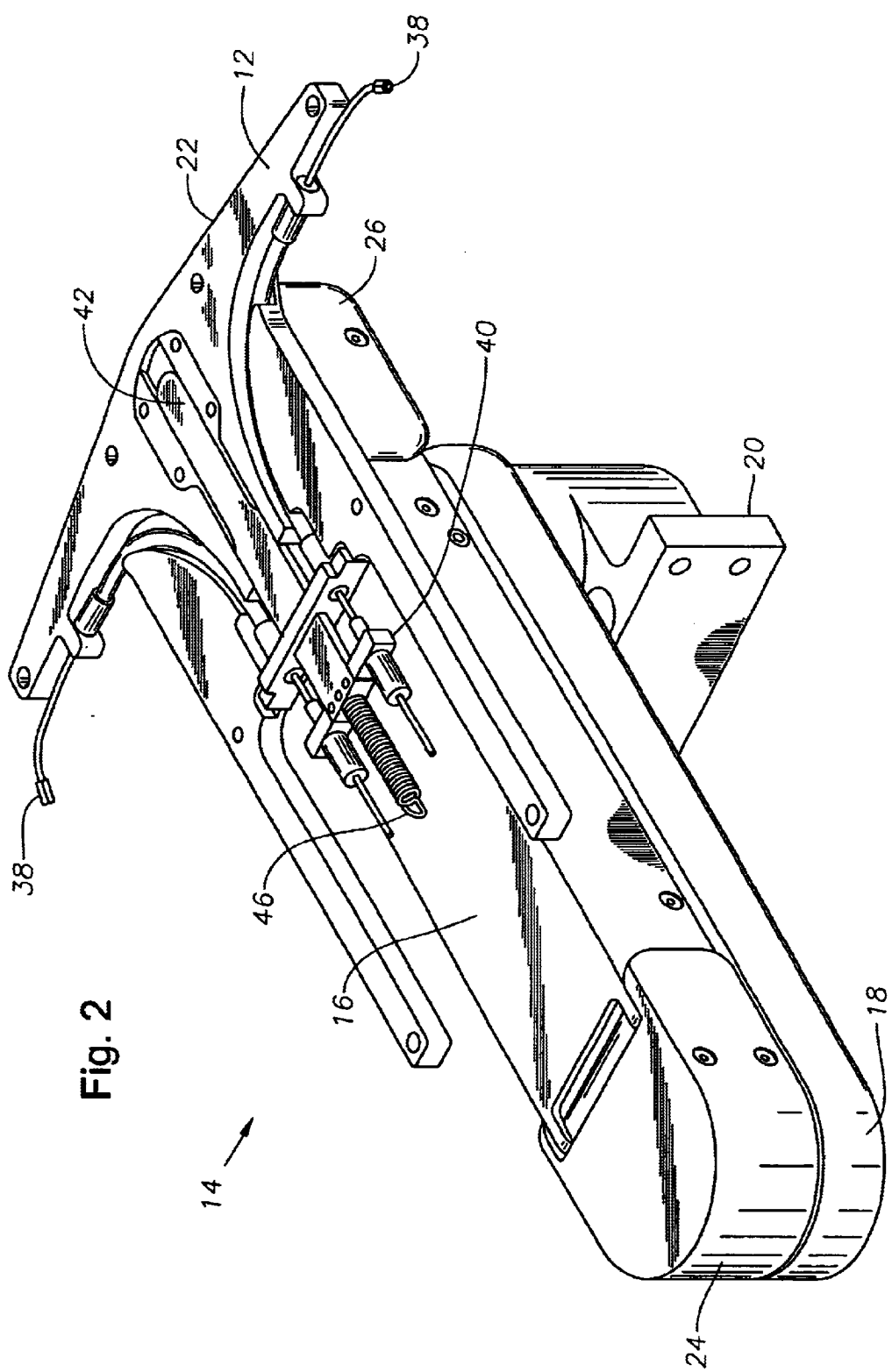
FIG. 2 is a perspective view of the assembled arm mechanism of the present invention.
Figure 4:
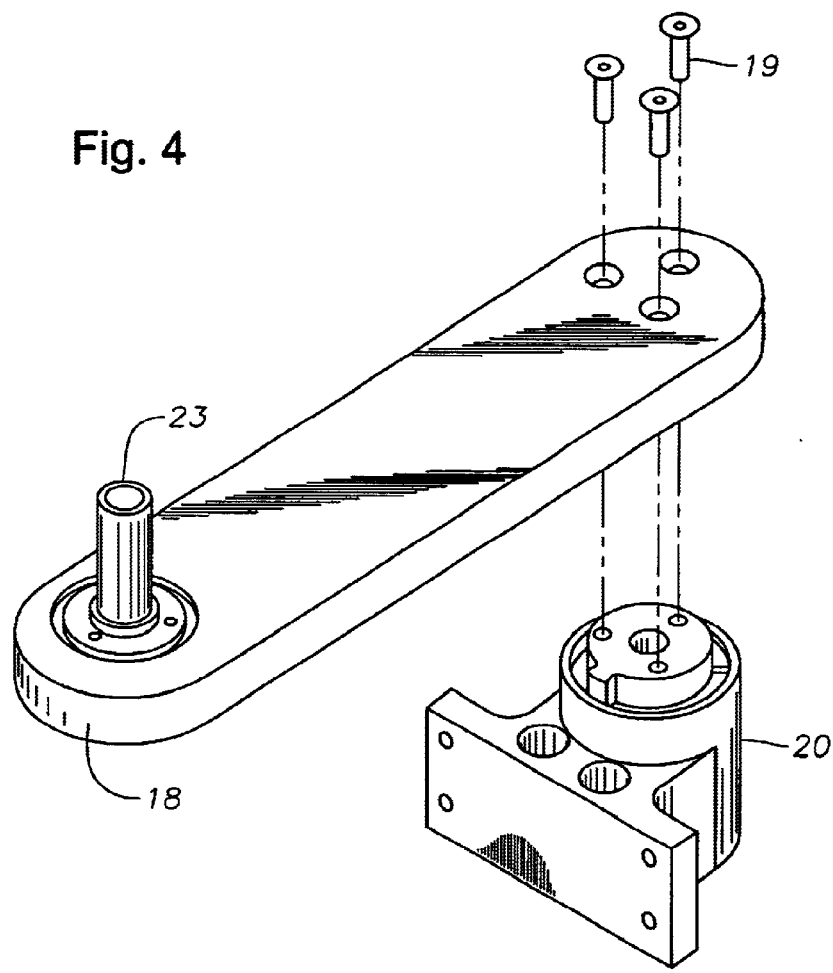
FIG. 4 is an exploded partial assembly view of the console pivoting mechanism used with the arm mechanism of the present invention.

As best seen in FIG. 2, arm mechanism 14 of the present invention generally includes upper arm 16, lower arm 18, pivoting console mount 20 and pivoting tray plate 22. As best seen in FIG. 4, lower arm 18 is rotatably connected by fasteners 19 to console mount 20 and console mount 20 is connected to console 100 in a manner and location well-known in the art. Upper arm 16 connects to lower arm 18 through pivot pin 23. Console mount allows lower arm 18 to pivot with respect to console 100, and pivot pin 23 allows upper arm 16 to rotate or pivot about lower arm 18.

Figure 3:
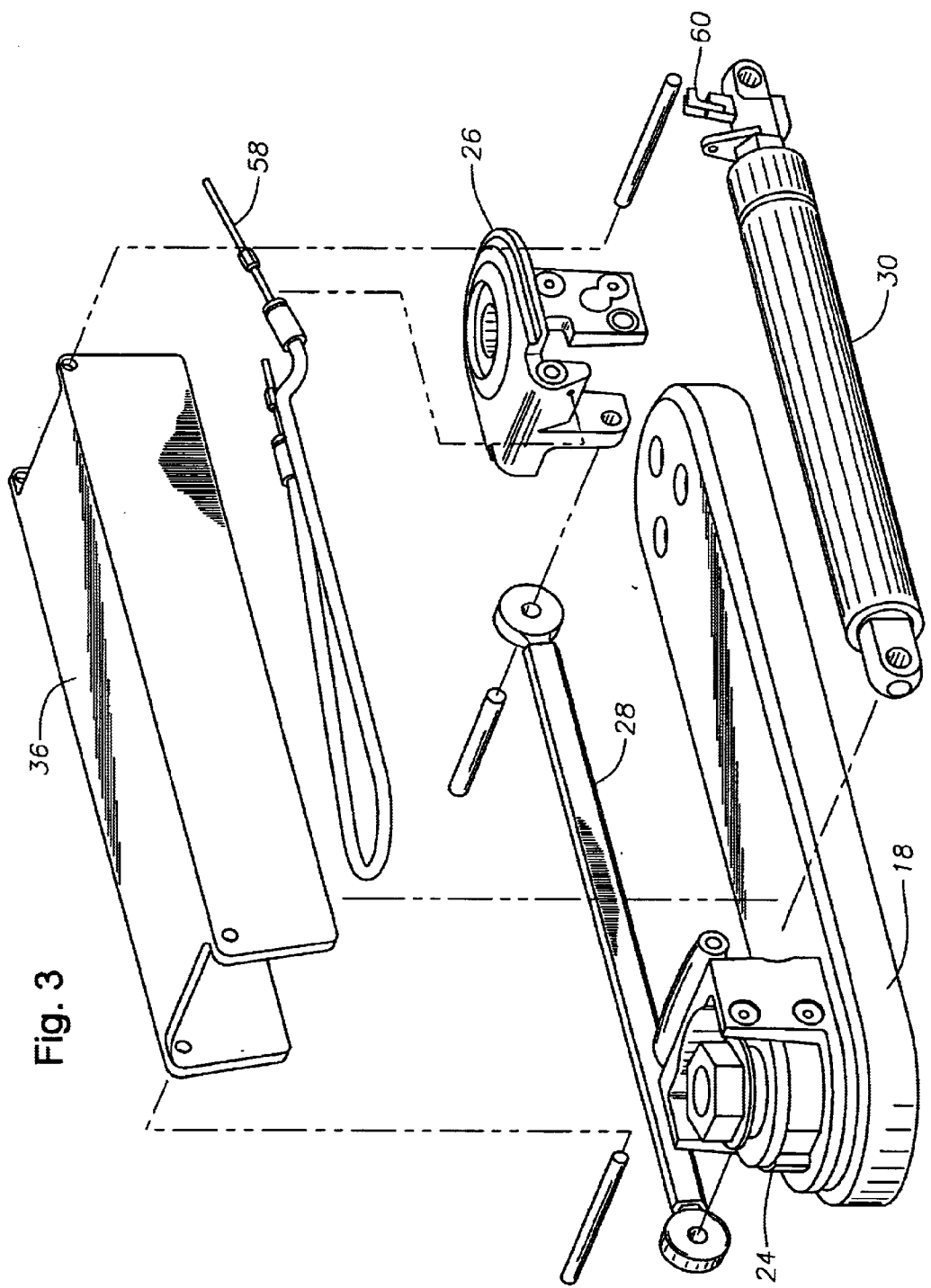
FIG. 3 is an exploded partial assembly view illustrating the height adjusting gas cylinder that may be used with the arm mechanism of the present invention.
Figure 6A:
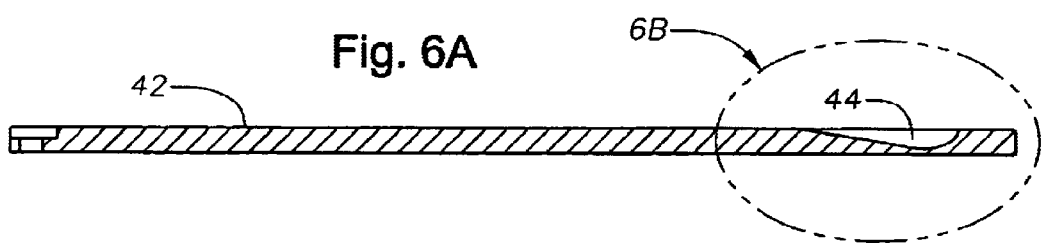
FIG. 6A is a cross-sectional view of the wedge plate used with the arm mechanism of the present invention.
Figure 6B:
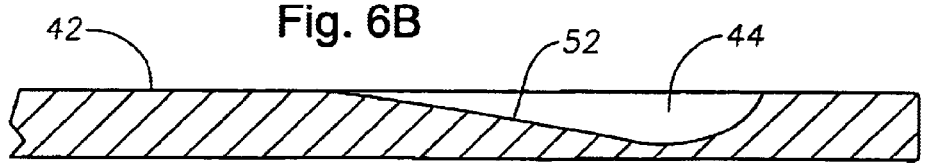
FIG. 6B is an enlarged, partial elevational view of the wedge plate used with the arm mechanism of the present invention taken at circle 6B in FIG. 6A.
Figure 5:
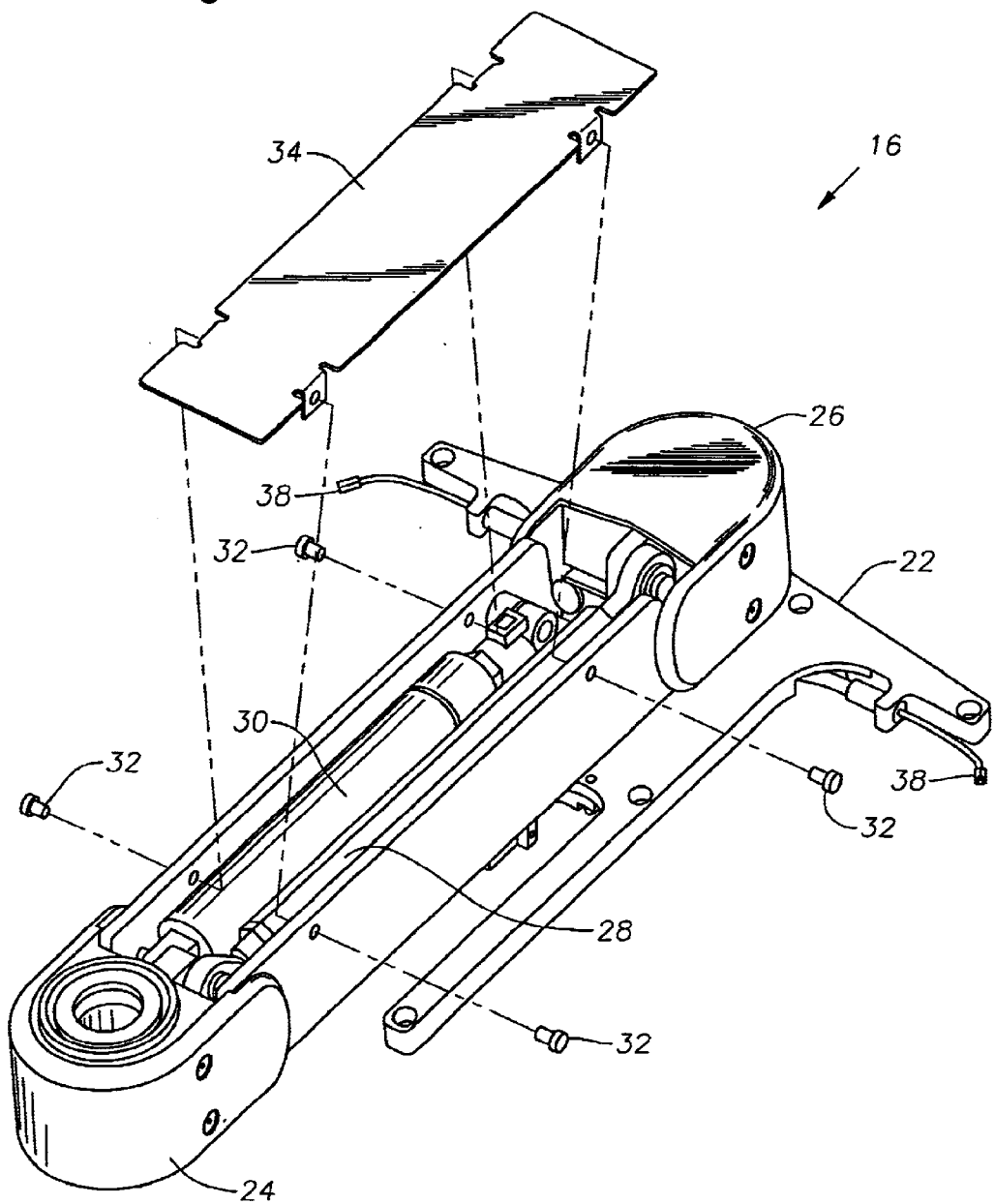
FIG. 5 is a bottom, partial assembly view of the upper arm portion of the arm mechanism of the present invention.

As best seen in FIGS. 3 and 5, upper arm 16 generally consists of lower arm pivot assembly 24, tray pivot assembly 26, lower strut rod 28, upper strut channel 36 and an position lockable gas spring 30. Upper strut channel 36 and lower strut rod 28 combine with lower arm pivot 24 and tray pivot 26 to form a 4 bar linkage. This linkage interrelationship between upper strut channel 36 and lower strut rod 28 allows elevational changes while maintaining parallelism between lower pivot assembly 24 and upper tray pivot 26. One end of spring 30 is attached to lower pivot assembly 24 and the other end of spring 30 is attached to upper strut channel 36. The position lockable feature of spring 30 provides the elevation retention for arm mechanism 14. Strut rod 28 and gas spring 30 are well-known in the art and commercially available from a variety of sources. Lower arm pivot assembly is received on pivot pin 23 on lower arm 18 and allows upper arm 16 to rotate relative to lower arm 18. Tray pivot assembly 26 allows tray plate 22 to rotate 360° relative to upper arm 16. Pivot assemblies 24 and 26 are of conventional design As best seen in FIG. 2, tray plate 22 contains actuation cables 38 that are attached to handles 12 on one end and to actuation bar 40 at the other end. Attached to actuation bar 40 spaced between cables 38, is wedge plate 42. As best seen in FIG. 6, wedge plate 42 is a long metal plate having sloped or ramped depression 44 on the underside of one end. Wedge plate 42 reciprocates within tray plate 22 by actuation of handles 12 pulling on cables 38, which pulls actuation bar 40 to which wedge plate 42 is attached. Return spring 46 causes actuation bar 40 to return to its rest position following release of handle 12.

Figure 7A:
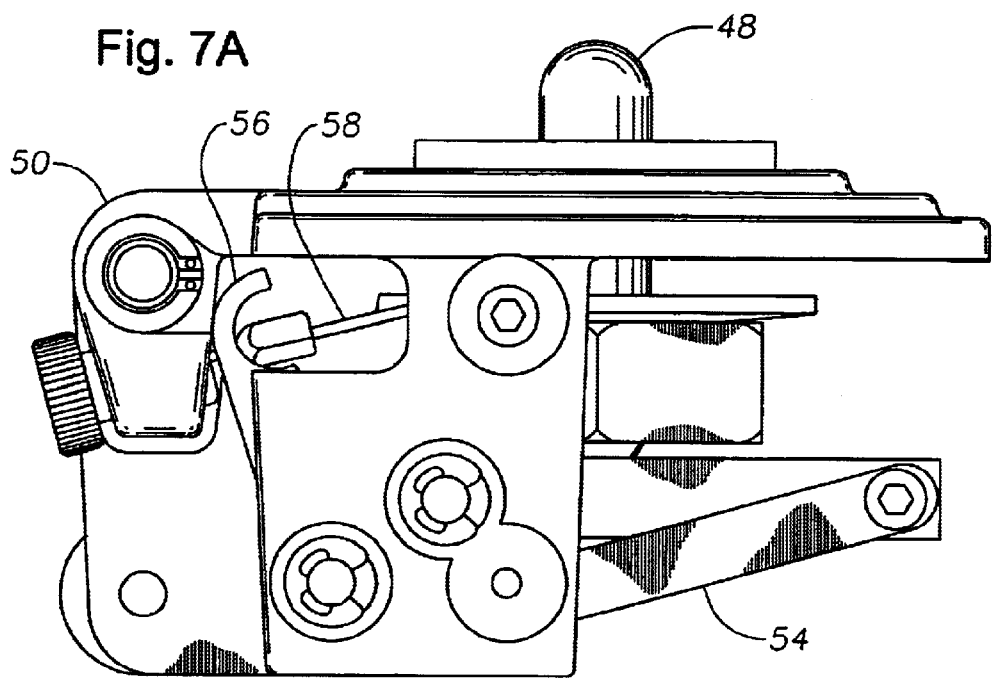
FIG. 7A is an enlarged perspective view of the actuation mechanism that may be used with the arm mechanism of the present invention showing the mechanism in the unactuated position.
Figure 7B:
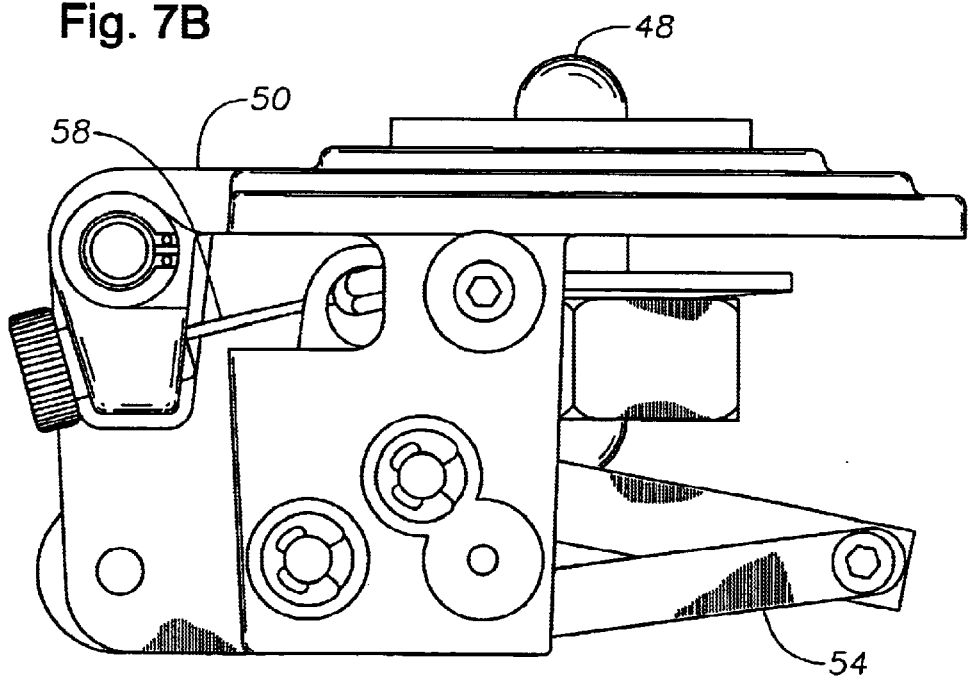
FIG. 7B is an enlarged perspective view of the actuation mechanism that may be used with the arm mechanism of the present invention showing the mechanism in the actuated position.

As best seen in FIGS. 7A and 7B, wedge plate 42 operates on motion transfer pin 48 of multi-lever actuation mechanism 50, which is mounted to tray pivot assembly 26 beneath wedge plate 42 so that pin 48 projects into depression 44. In use, the horizontal sliding movement of wedge plate 42 causes an elevational change to motion transfer pin 48 as pin 48 rides up ramp 52 of wedge plate 42. The vertical motion of pin 48 forces down lever mechanism 54 causing cable pull 56 to move from its initial position shown in FIG. 7A into its actuated position, shown in FIG. 7B. Such movement results in movement of cable 58.

As best seen in FIG. 3, the other end of cable 58, opposite cable pull 56, is attached to actuation lever 60 on spring 30. Movement of cable 58 causes a corresponding rotation of lever 60, allowing extension or retraction of spring 30. Extension of spring 30 causes upper arm 16 to pivot upward relative to lower arm 18, and pressing on tray 10 while lever 60 is disengaged allows spring 30 to be compressed, thereby lowering upper arm 16 relative to lower arm 18.

In use, actuation of handle 12 causes wedge plate 42 to slide forward. As wedge plate slides forward, pin 48 rides up sloped portion 52 of depression 44, pushing pin 48 downward. Downward pressure on pin 48 forces down mechanism 54, thereby moving cable 58 and rotating actuation lever 60.

This description is given for purposes of illustration and explanation. It will be apparent to those skilled in the relevant art that changes and modifications may be made to the invention described above without departing from its scope or spirit.

I claim:

1. An arm mechanism for a surgical tray, comprising:
   a) a rotatable lower arm;
   b) an upper arm pivotally and rotatably mounted to the lower arm;
   c) a tray mount rotatably mounted to the upper arm opposite the lower arm so as to allow the tray mount to be raised or lowered relative to the lower arm;
   d) an extendable, position lockable gas spring connected to the tray mount so as to assist in the raising of the tray mount and the holding of a vertical position of the tray mount relative to the lower arm;
   e) an actuation lever on the gas spring to hold the gas spring in a plurality of extended positions; and
   f) a means for moving the actuation lever.

2. The mechanism of claim 1 wherein the means for moving the actuation lever includes a sliding wedge plate operating to depress a motion transfer pin.

3. The mechanism of claim 1 wherein the means for moving the actuation lever includes a cable connected to the actuation lever on one end, and to a multi-lever mechanism actuated by depressing a motion transfer pin on the other end.

4. An arm mechanism for a surgical tray, comprising:
   a) a lower arm;
   b) an upper arm pivotally and rotatably mounted to the lower arm;
   c) a pivoting tray mount rotatably mounted to the upper arm opposite the lower arm so that the pivoting tray mount can be raised or lowered relative to the lower arm;
   d) a position lockable gas spring connected to the pivoting tray mount so as to assist in the raising of the pivoting assembly relative to the lower arm;
   e) an actuation lever on the gas spring to hold the gas spring in a plurality of extended positions; and
   f) a means for moving the actuation lever, the means including a sliding wedge plate operating to depress a motion transfer pin and a cable connected to the actuation lever on one end and to a multi-lever mechanism actuated by depressing the motion transfer pin on the other end.

* * * * *